(12) United States Patent
Ordway

(10) Patent No.: US 6,331,170 B1
(45) Date of Patent: Dec. 18, 2001

(54) ADJUSTABLE BACK SUPPORT

(76) Inventor: Griffin Ordway, 662 Matagual Dr., Vista, CA (US) 92083

( * ) Notice: Subject to any disclaimer, the term of this patent is extended or adjusted under 35 U.S.C. 154(b) by 0 days.

(21) Appl. No.: 09/586,631

(22) Filed: Jun. 5, 2000

(51) Int. Cl.[7] .................................................. A61F 5/00
(52) U.S. Cl. .............................. 602/19; 128/876; 602/13
(58) Field of Search .................................. 128/846, 869, 128/870, 874, 875, 876; 602/19, 13

(56) References Cited

U.S. PATENT DOCUMENTS

| | | | |
|---|---|---|---|
| 4,135,503 | * 1/1979 | Romano | 602/19 |
| 5,195,948 | * 3/1993 | Hill | 602/19 |
| 5,396,906 | * 3/1995 | Harrold | 128/876 |
| 5,547,461 | * 8/1996 | Levis | 602/13 |
| 5,628,721 | * 5/1997 | Arnold | 602/19 |

* cited by examiner

Primary Examiner—Michael A. Brown

(57) ABSTRACT

A method and system for an inflatable, adjustable back support is disclosed. Preferably, the back support resembles a fanny pack. The fanny pack includes an inflatable bladder which is encased in the fanny pack pouch. A pump is provided for inflating the bladder. A deflation device (e.g., release valve) is provided for deflating the bladder. The pump may be encased in a small pouch.

8 Claims, 5 Drawing Sheets

ADJUSTABLE BACK SUPPORT

FIELD OF THE INVENTION

This invention relates generally to back supports and, more particularly, to an inflatable, adjustable, back support.

BACKGROUND OF THE INVENTION

Back pain or fatigue is a fact of life that plagues a large percentage of society. Many factors can contribute to back fatigue, for example stress or simply remaining in a seated or awkward position for extended periods of time.

Many devices have been used over time to combat back fatigue. For example, an ordinary pillow may be placed behind the back. However, an ordinary pillow has many disadvantages. For example, it is extremely difficult to find a properly fitted pillow for an individual. And even if an individual does find a pillow that is perfectly fitted at a given time, the pillow may not be appropriate for the individual at all times. Therefore, a need exists for an adjustable back support pillow.

U.S. Pat. No. 4,622,957 issued to J. D. Curlee for a therapeutic corset attempted to satisfy this need. The therapeutic corset consists of an elongated rigid or semi-rigid support surface formed of a bendable material. The support surface includes a flexible bladder for retaining fluids. A disadvantage of this and similar devices is that they are adjustable by filling a bladder with fluid. It can be time-consuming and inconvenient to add or remove fluid from the bladder.

U.S. Pat. No. 5,228,609 issued to Gregory discloses a fanny pack which includes a back support section including a lumbar pad composed of pieces of polyfoam. Although the fanny pack style has the advantage of being portable and inconspicuous, it has the disadvantage of not being adjustable.

Adjustable back support devices include inflatable lumbar support devices which can be found in vehicle seats (for example, U.S. Pat. No. 5,658,050 issued to J. R. Lorbiecki), office chairs and backpacks (U.S. Pat. No. 5,547,461 issued to J. D. Levis). These devices provide adjustable support, however, they are not inconspicuous.

The present invention addresses the above problem by incorporating an inflatable bladder in a fanny pack and a pump in a side pouch, thereby providing an inconspicuous, adjustable, and highly portable back support device.

SUMMARY OF THE INVENTION

The present invention is directed to an inflatable, adjustable back support. Preferably, the back support resembles a fanny pack, thus being portable and inconspicuous.

The fanny pack of the present invention includes a pouch and a strap. The strap is like the straps found on normal fanny packs and is adjustable to fit around the waist of a wearer. However, unlike normal fanny packs, an inflatable bladder is located inside the pouch.

A small pump is provided for inflating the bladder located in the pouch. The pump includes a release valve for deflating the bladder. Preferably, the pump is enclosed in a separate carrying pouch which slips onto the strap supporting the pouch.

DESCRIPTION OF THE SPECIFIC EMBODIMENT

Figure 1:
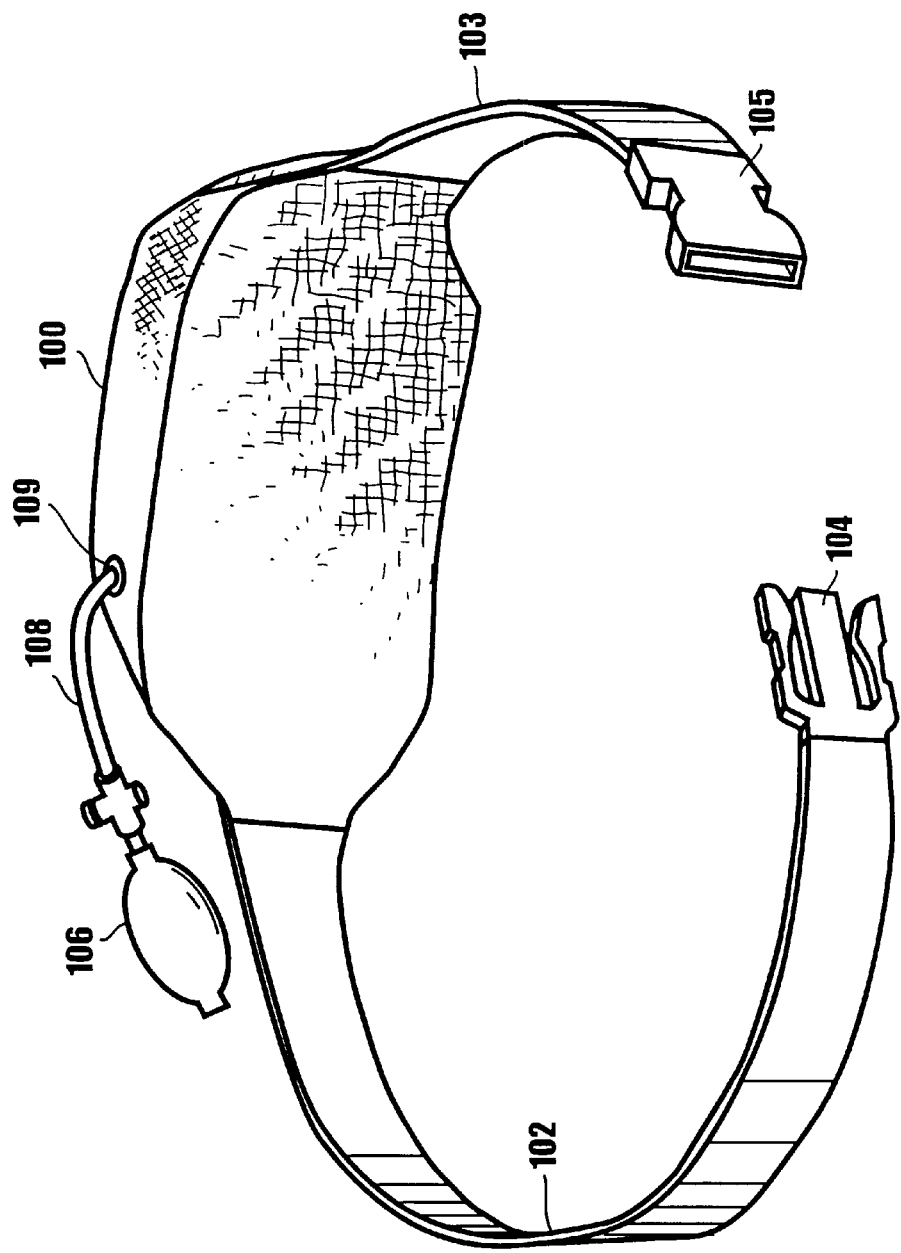
FIG. 1 is a perspective view of the present inflatable back support.

FIG. 1 illustrates a perspective view of the inflatable back support of the present invention. The back support includes an inflatable back support member 100. The back support member 100 is inflated using a pump 106. Pump 106 dispenses air to back support member 100 via a hose 108. In a preferred embodiment, back support member 100 includes an enclosed inflatable bladder (not shown). In a preferred embodiment, the bladder is made of plastic material. However, it will be appreciated that other materials which are strong, yet flexible, such as rubber may be used. In addition, the back support member 100 may itself be the inflatable member provided it is air tight. In such a case the zipper would be omitted. The hose 108 is threaded through a hole 109 in order to attach the enclosed bladder to the pump 106 which is in a location which is external to the enclosed bladder.

Figure 2:
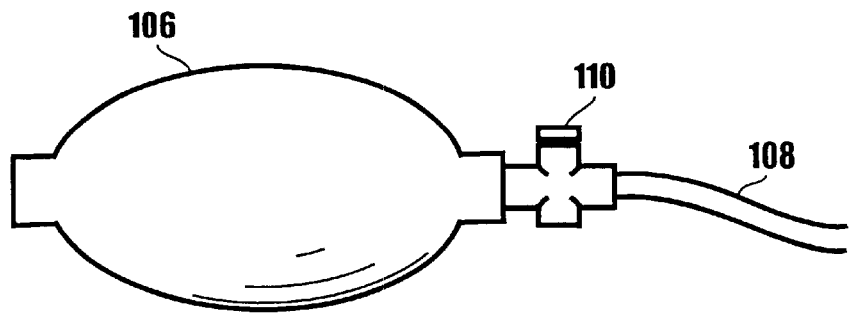
FIG. 2 illustrates the inflation/deflation device of the present invention.

Integral to pump 106 is a deflation device 110 as shown in FIG. 2. The deflation device 110 shown in FIG. 2 is a release valve. The deflation device 110 works in the same manner as the release valve located in a tire stem. Applying pressure to (i.e., pressing) the release valve causes the valve to open and pressurized air to escape the bladder. When the pressure is released (i.e. no longer pressing the release valve), the valve again closes and the release of air ceases.

Figure 3:
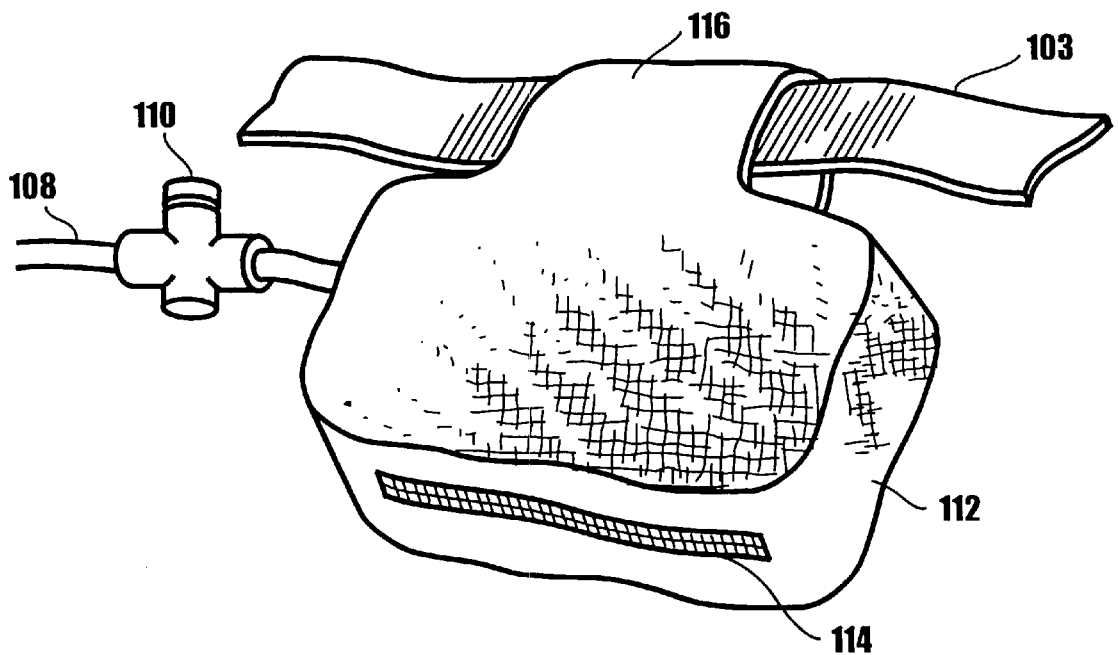
FIG. 3 illustrates the inflation/deflation device of FIG. 2 enclosed in a pouch.

The pump may be enclosed in a pouch 112 as shown in FIG. 3. The enclosure may contain an opening, such as zipper 114. An opening is not required since the pump can be activated through the pouch. However, an opening, such as that of zipper 114 is desirable as it allows easy access should the pump ever require maintenance or replacement. The pouch 112 is attached to a strap 116 which can be looped around strap 103 as shown. The pouch 112 may alternatively be looped around strap 102 for placement on either side of the user's body. For example, the pump may be located on the right side for right-handed people while an alternative embodiment may have the pump located on the left side for left-handed people.

The back support shown in FIG. 1 which includes the two straps 102 and 103, also includes connectors 104 and 105 located on straps 102 and 103, respectively. Connectors 104 and 105 are mating connectors which can be attached to each other. In a preferred embodiment connectors 104 and 105 are a pronged connector which engages in a hollow connector. The connectors can be made out of various materials, such as plastic or metal. A preferred connector is the type of connector found on fanny packs, as shown in detail in FIG. 2.

Figure 4:
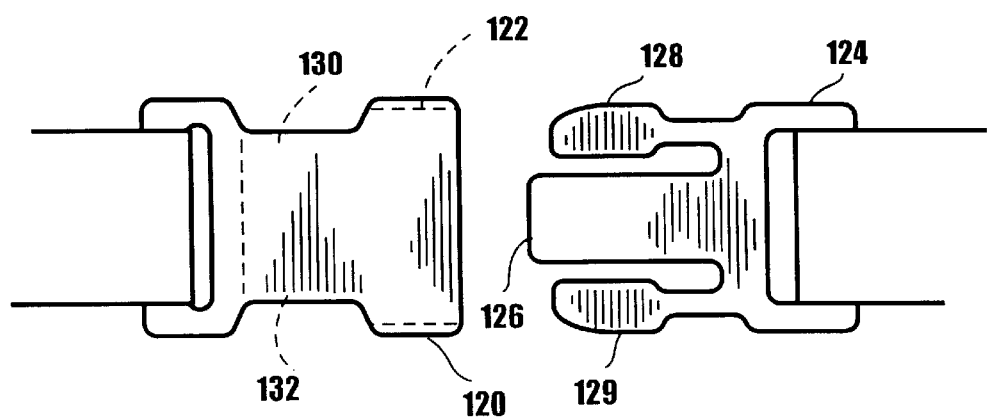
FIG. 4 is an example of an unlatched connector included in a preferred embodiment of the present invention.

The connector illustrated in FIG. 4 includes a receiving connector 120 which includes an opening 122 for receiving an engaging connector 124. The engaging connector 124 includes a main prong 126 which is located at center position at the end of the engaging connector 124. The main prong is fairly rigid. There are two end prongs 128 and 129 located on opposite sides of the main prong. The end prongs 128 and 129 are flexible so that they can be pressed inwardly to insert the engaging connector 124 into the receiving connector 120 but sufficiently resilient to engage the receiving connector 120 when released. Once the prongs 126, 128 and 129 are inside the opening 122 of the receiving connector 120, they flex outwardly to their original position so that the connector latches in place as shown in FIG. 3.

Figure 5:
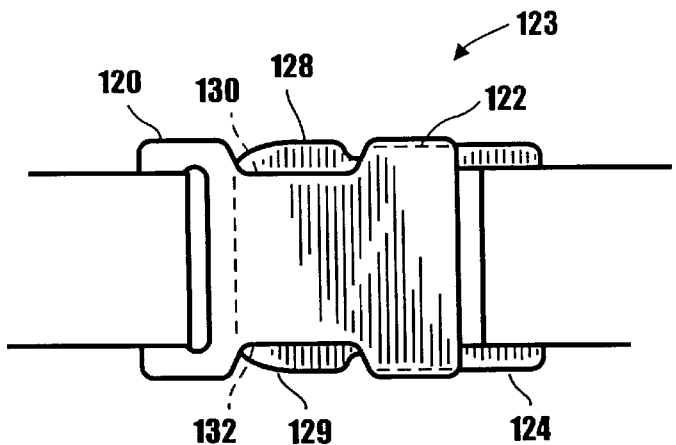
FIG. 5 illustrates the connector of FIG. 2 in a latched position.

Receiving connector 120 also has side openings 130 and 132. As shown in FIG. 5, when the connector is latched, the end prongs 128 and 129 can be accessed via the side openings 130 and 132. The connector can be unlatched by pressing prongs 128 and 129 inwardly.

Figure 6:
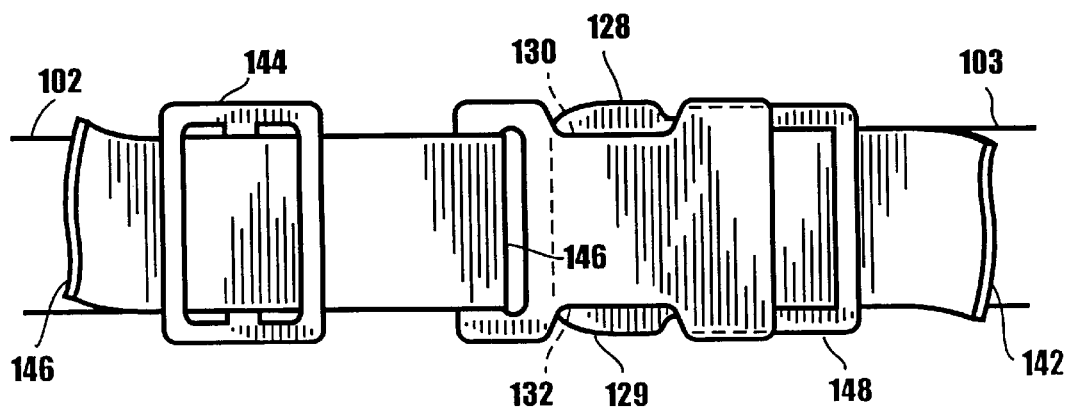
FIG. 6 illustrates the latched connector of FIG. 3 connected to adjustable straps.

The latched connector shown in FIG. 5 is shown in FIG. 6 along with straps 102 and 103 which are connected to the receiving connector 120 and the engaging connector 124, respectively. Strap 102 is looped through adjustment buckle 144 before and after being looped through receiving connector bar 146. Adjustment buckle 144 allows strap 102 to be adjusted in length (i.e., shortened or lengthened). Strap 103 may be adjusted instead of or in addition to strap 102. In one embodiment an adjustment buckle such as adjustment buckle 144 is used to adjust strap 103. In an alternative embodiment, as shown in FIG. 4, the adjustment buckle 148 can be integral to the engagement connector 124. Similarly, an adjustment buckle could be integral to the engagement connector 120.

The connector shown is illustrative and other types of connectors may be used. For example, a belt buckle style connector, snaps, or Velcro may be used as a connector, as well as other types of connectors. Alternatively there may not be a connector. Instead of two straps which are attached using a connector, there could be a single strap, for example an elasticized strap.

Figure 7:
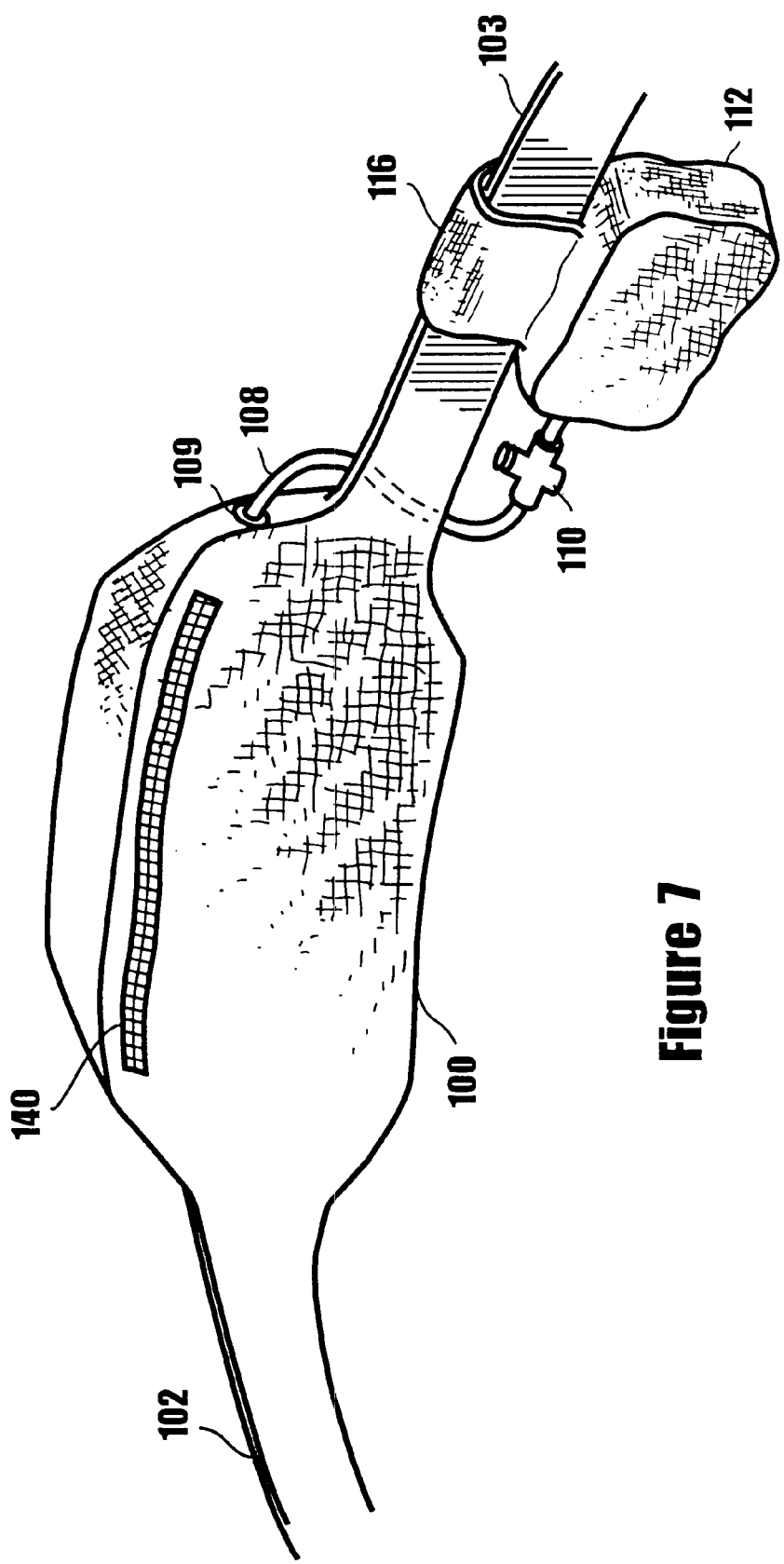
FIG. 7 is a perspective view of a preferred embodiment of present inflatable back support.

FIG. 7 illustrates a perspective view of a preferred embodiment of the back support of the present invention. The back support is in the style of a fanny pack. The embodiment illustrated in FIG. 7 is in the shape of an elongated octagon, however other shapes are possible. In a preferred embodiment, the back support member 100 is approximately 12 inches in length and six inches in height. The back support member 100 can be made of various elastic or partially elastic materials, such as, neoprene which is preferred. The selection of the material of the back support 100 from stretchable material provides additional flexibility in the application of the invention. Elastic material permits inflating while also allowing the back support to act as a corset due to its longitudinal elasticity. Alternatively, the material may be non-stretchable to provide a binding support. Back support member 100 may contain an opening 140, such as a the zippered opening as shown in FIG. 7 for permitting access to the bladder.

Figure 8:
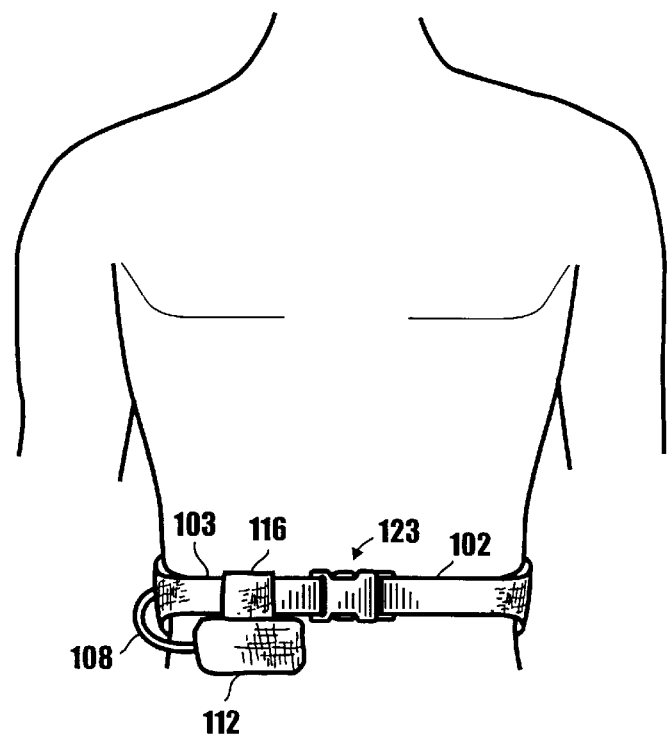
FIG. 8 illustrates a front view of a person wearing the back support of the present invention.
Figure 9:
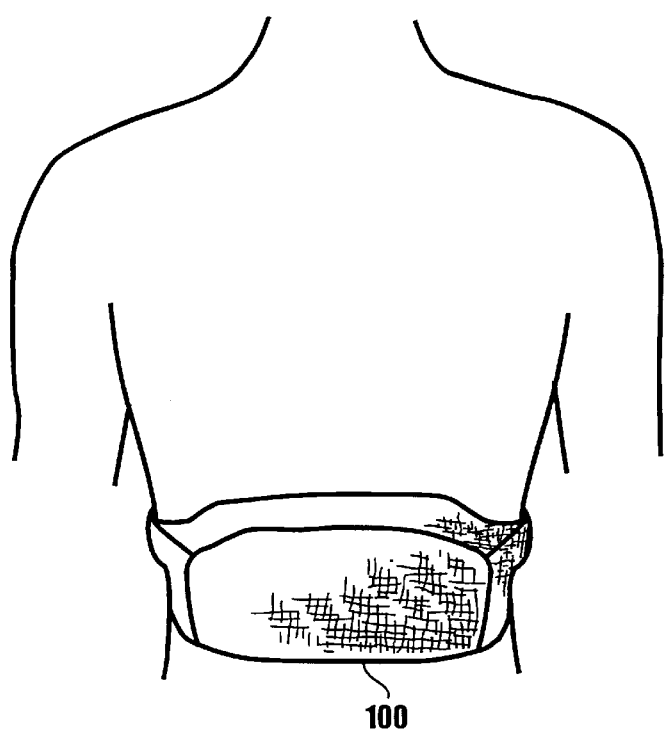
FIG. 9 illustrates a rear view of a person wearing the back support of the present invention.

FIGS. 8 and 9 illustrate a front and rear view, respectively, of the back support in use. As shown, the back support is inconspicuous because it resembles an ordinary fanny pack. Thus, the wearer has an adjustable, portable, inconspicuous back support which may be worn while seated (e.g., in a car, on a chair, etc.), while standing, while walking or even while lying down. The back support member can be inflated and deflated as desired by the user. This permits the user to inflate the bladder to permit the back support member to apply pressure and simply by releasing some of the air to adjust the pressure to that which is comfortable or desirable by the user. The selected pressure will then remain until the user wishes to either increase the pressure or decrease the pressure by inflation or deflation as the case may be. Additionally, the back support member can be positioned to apply pressure to any particular location on the body as desired, e.g., center of back, to one side, etc.

While a specific embodiment of this invention has been described above, those skilled in the art will readily appreciate that many modifications are possible in the specific embodiment, without materially departing from the novel teachings and advantages of this invention. Accordingly, all such modifications are intended to be included within the scope of this invention, as defined in the following claims.

Having thus described the invention, what is claimed is:

1. A back support comprising:
   a. an elongated elastic back support member, having first and second longitudinal ends disposed along the longitudinal axis of said elongated member, said back support member being stretchable in at least the longitudinal direction and forming an enclosure;
   b. an inflatable apparatus received within the enclosure of said back support member;
   c. a controllable inflating apparatus for inflating said inflatable apparatus coupled to said inflatable apparatus; and
   d. at least one strap, having a first end and a second end, said first end being connected to said first longitudinal end of said elongated back support member and said second end being connected to said second longitudinal end of said elongated back support member, wherein said second side of said back support member is connected opposite said first side of said back support member.
   e. a pump for inflating said inflatable device, wherein said pump slideably engages said strap for selective positioning of said pump along said strap.

2. The back support of claim 1 wherein said pump is enclosed in a housing which slideably engages said strap.

3. The back support of claim 2 wherein said housing is a pouch.

4. The back support of claim 1 further comprising a deflation apparatus for deflating said inflatable apparatus.

5. The back support of claim 4 wherein said deflation device is integral to said pump.

6. A method for providing back support using the back support device as described in claim 4, said method comprising:
   a. placing said back support device in a position such that said back support member is adjacent to the location of a users body for which support is desired;
   b. fastening said strap to said back support around the users body; and
   c. inflating said support device a desired amount using said pump.

7. The method for providing back support as described in claim 6 further comprising the additional step of deflating the inflatable apparatus a desired amount using said deflation apparatus.

8. A back support comprising:
   a. an elongated elastic back support member, having first and second longitudinal ends disposed along the longitudinal axis of said elongated member, said back support member being stretchable in at least the longitudinal direction and forming an enclosure;
b. an inflatable apparatus received within the enclosure of said back support member;
c. a controllable inflating apparatus for inflating, said inflatable apparatus coupled to said inflating apparatus; and
d. a plurality of straps further comprising:
   i. at least one first strap, having a first end and a second end, wherein said first strap first end is attached to said first side of said longitudinal end of said elongated back support member; and
   i. at least one second strap having a first end and a second end, wherein said second strap first end is attached to said second side of said longitudinal end of said elongated back support member and said second strap second end is attached to said first strap second end, and
e. a pump for inflating said inflatable device, wherein said pump slideably engages at least one of said straps for selective positioning of said pump along said engaged strap.

* * * * *